United States Patent [19]
Reznikoff et al.

[11] Patent Number: 5,965,443
[45] Date of Patent: *Oct. 12, 1999

[54] SYSTEM FOR IN VITRO TRANSPOSITION

[75] Inventors: William S. Reznikoff, Maple Bluff; Igor Yu Goryshin, Madison, both of Wis.

[73] Assignee: Wisconsin Alumni Research Foundation, Madison, Wis.

[*] Notice: This patent is subject to a terminal disclaimer.

[21] Appl. No.: 08/814,877

[22] Filed: Sep. 9, 1996

[51] Int. Cl.$^6$ .......................... C12N 15/74; C07K 13/00; C07H 21/04
[52] U.S. Cl. .................. 435/473; 530/350; 536/23.1; 536/24.1
[58] Field of Search .............................. 435/6, 69.2, 193, 435/473; 530/350, 808; 536/23.1, 24.1

[56] References Cited

PUBLICATIONS

Benjamin, Howard W., "Excision of Tn10 from the donor site during transposition occurs by flush double–strand cleavages at the transposon termini," *Proc. Natl. Acad. Sci. USA*, 89:4648–4652 (May 1992).
Craigie, Robert, et al., "A defined system for the DNA strand–transfer reaction at the initiation of bacteriophage Mu transposition: Protein and DNA substrate requirements," *Proc. Natl. Acad. Sci. USA*, 82:7570–7574 (Nov. 1985).
de la Cruz, Norberto B., et al., "Characterization of the TN5 Transposase and Inhibitor Proteins: a Model for the Inhibition of Transposition," *Journal of Bacterioilogy*, 175(21):6932–6938 (Nov. 1993).
Jilk, Ross Alan, et al., "The Organization for the Outside End of Transposon Tn5," *Journal of Bacteriology*, 178(6):1671–1679 (Mar. 1996).
Lavoie, B.D., et al., "Transposition of Phage Mu DNA," Dept. of Biochemistry, Jniv. of Western Ontario. Current Topics in Microbiol and Immunol., vol. 204:83–102 (1995).
Mizuuchi, Kiyoshi, "In Vitro Transposition of Bacteriophage Mu: A Biochemical Approach to a Novel Replication Reaction," *Cell*, 35:785–794 (Dec. 1983).
Morisata, Donald, et al., "TN10 Transposition and Circle Formation In Vitro," *Cell*, 51:101–111 (Oct. 9, 1987).
Sakai, Janice, et al., "Identification and characterization of a pre–cleavage synaptic complex that is an early intermediate in TN10 transposition," *The EMBO Journal*, 14(17):4374–4383 (1995).
Weinreich, Michael D., "A Functional Analysis of the TN5 Transposase: Identification of Domains Required for DNA Binding and Multimerization," *J. Mol. Biol.*, 241:166–177 (1994).
Weinreich, Michael D., et al., "Evidence that the cis preference of the Tn5 transposase is caused by nonproductive multimerization," *Genes & Development*, 8:2363–2374 (1994).
Wiegand, Torsten W., et al., "Characterization of Two Hypertransposing Tn5 Mutants," *Journal of Bacteriology*, 174(4):1229–1239 (Feb. 1992).
DeLong, A., et al., "Trans–Acting Transposase Mutant From Tn5," *Proc. Natl. Acad. Sci. USA*, 88:6072–6076 (1991).
Johnson, R.C., et al., "DNA Sequences at the Ends of Transposon Tn5 Required for Transposition," *Nature* 304:280–282 (1983).
Weigand, Torsten Walter, "Transposase Mutants That Increase the Transposition Frequency of Tn5 (*Escherichia Coli*)," Thesis abstract (1993).
Zhou, M., et al., "Three Types of Novel Mutations in the $NH_2$–Terminus of Tn5 Transposase: Structure/Function," Keystone Symposium abstract (1994), Supp 18B, p. 45 Journal of Cell Biology.

*Primary Examiner*—James Ketter
*Assistant Examiner*—William Sandals
*Attorney, Agent, or Firm*—Quarles & Brady LLP

[57] ABSTRACT

A system for in vitro transposition includes a donor DNA that includes a transposable element flanked by a pair of bacterial transposon Tn5 outside end repeat sequences, a target DNA into which the transposable element can transpose, and a modified Tn5 transposase having higher binding avidity to the outside end repeat sequences and being less likely to assume an inactive multimer form than wild type Tn5 transposase.

21 Claims, 3 Drawing Sheets

5,965,443

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
      (A) LENGTH: 1534 base pairs
      (B) TYPE: nucleic acid
      (C) STRANDEDNESS: double
      (D) TOPOLOGY: linear (ii) MOLECULE TYPE: other nucleic acid
      (A) DESCRIPTION: /desc = "Gene encoding modified Tn5
          transposase enzyme"

(ix) FEATURE:
      (A) NAME/KEY: CDS
      (B) LOCATION: 93..1523

(xi) SEQUENCE DESCRIPTION: SEQ ID NO:1:

```
CTGACTCTTA TACACAAGTA GCGTCCTGAA CGGAACCTTT CCCGTTTTCC AGGATCTGAT        60

CTTCCATGTG ACCTCCTAAC ATGGTAACGT TC ATG ATA ACT TCT GCT CTT CAT         113
                                   Met Ile Thr Ser Ala Leu His
                                     1               5

CGT GCG GCC GAC TGG GCT AAA TCT GTG TTC TCT TCG GCG GCG CTG GGT         161
Arg Ala Ala Asp Trp Ala Lys Ser Val Phe Ser Ser Ala Ala Leu Gly
            10                  15                  20

GAT CCT CGC CGT ACT GCC CGC TTG GTT AAC GTC GCC GCC CAA TTG GCA         209
Asp Pro Arg Arg Thr Ala Arg Leu Val Asn Val Ala Ala Gln Leu Ala
 25                  30                  35

AAA TAT TCT GGT AAA TCA ATA ACC ATC TCA TCA GAG GGT AGT AAA GCC         257
Lys Tyr Ser Gly Lys Ser Ile Thr Ile Ser Ser Glu Gly Ser Lys Ala
 40                  45                  50                  55

GCC CAG GAA GGC GCT TAC CGA TTT ATC CGC AAT CCC AAC GTT TCT GCC         305
Ala Gln Glu Gly Ala Tyr Arg Phe Ile Arg Asn Pro Asn Val Ser Ala
                 60                  65                  70

GAG GCG ATC AGA AAG GCT GGC GCC ATG CAA ACA GTC AAG TTG GCT CAG         353
Glu Ala Ile Arg Lys Ala Gly Ala Met Gln Thr Val Lys Leu Ala Gln
             75                  80                  85

GAG TTT CCC GAA CTG CTG GCC ATT GAG GAC ACC ACC TCT TTG AGT TAT         401
Glu Phe Pro Glu Leu Leu Ala Ile Glu Asp Thr Thr Ser Leu Ser Tyr
         90                  95                 100

CGC CAC CAG GTC GCC GAA GAG CTT GGC AAG CTG GGC TCT ATT CAG GAT         449
Arg His Gln Val Ala Glu Glu Leu Gly Lys Leu Gly Ser Ile Gln Asp
    105                 110                 115

AAA TCC CGC GGA TGG TGG GTT CAC TCC GTT CTC TTG CTC GAG GCC ACC         497
Lys Ser Arg Gly Trp Trp Val His Ser Val Leu Leu Leu Glu Ala Thr
120                 125                 130                 135

ACA TTC CGC ACC GTA GGA TTA CTG CAT CAG GAG TGG TGG ATG CGC CCG         545
Thr Phe Arg Thr Val Gly Leu Leu His Gln Glu Trp Trp Met Arg Pro
                140                 145                 150

GAT GAC CCT GCC GAT GCG GAT GAA AAG GAG AGT GGC AAA TGG CTG GCA         593
Asp Asp Pro Ala Asp Ala Asp Glu Lys Glu Ser Gly Lys Trp Leu Ala
            155                 160                 165

GCG GCC GCA ACT AGC CGG TTA CGC ATG GGC AGC ATG ATG AGC AAC GTG         641
Ala Ala Ala Thr Ser Arg Leu Arg Met Gly Ser Met Met Ser Asn Val
        170                 175                 180

ATT GCG GTC TGT GAC CGC GAA GCC GAT ATT CAT GCT TAT CTG CAG GAC         689
Ile Ala Val Cys Asp Arg Glu Ala Asp Ile His Ala Tyr Leu Gln Asp
    185                 190                 195
```

```
AGG CTG GCG CAT AAC GAG CGC TTC GTG GTG CGC TCC AAG CAC CCA CGC         737
Arg Leu Ala His Asn Glu Arg Phe Val Val Arg Ser Lys His Pro Arg
200                 205                 210                 215

AAG GAC GTA GAG TCT GGG TTG TAT CTG ATC GAC CAT CTG AAG AAC CAA         785
Lys Asp Val Glu Ser Gly Leu Tyr Leu Ile Asp His Leu Lys Asn Gln
                    220                 225                 230

CCG GAG TTG GGT GGC TAT CAG ATC AGC ATT CCG CAA AAG GGC GTG GTG         833
Pro Glu Leu Gly Gly Tyr Gln Ile Ser Ile Pro Gln Lys Gly Val Val
                235                 240                 245

GAT AAA CGC GGT AAA CGT AAA AAT CGA CCA GCC CGC AAG GCG AGC TTG         881
Asp Lys Arg Gly Lys Arg Lys Asn Arg Pro Ala Arg Lys Ala Ser Leu
        250                 255                 260

AGC CTG CGC AGT GGG CGC ATC ACG CTA AAA CAG GGG AAT ATC ACG CTC         929
Ser Leu Arg Ser Gly Arg Ile Thr Leu Lys Gln Gly Asn Ile Thr Leu
    265                 270                 275

AAC GCG GTG CTG GCC GAG GAG ATT AAC CCG CCC AAG GGT GAG ACC CCG         977
Asn Ala Val Leu Ala Glu Glu Ile Asn Pro Pro Lys Gly Glu Thr Pro
280                 285                 290                 295

TTG AAA TGG TTG TTG CTG ACC GGC GAA CCG GTC GAG TCG CTA GCC CAA        1025
Leu Lys Trp Leu Leu Leu Thr Gly Glu Pro Val Glu Ser Leu Ala Gln
                    300                 305                 310

GCC TTG CGC GTC ATC GAC ATT TAT ACC CAT CGC TGG CGG ATC GAG GAG        1073
Ala Leu Arg Val Ile Asp Ile Tyr Thr His Arg Trp Arg Ile Glu Glu
                315                 320                 325

TTC CAT AAG GCA TGG AAA ACC GGA GCA GGA GCC GAG AGG CAA CGC ATG        1121
Phe His Lys Ala Trp Lys Thr Gly Ala Gly Ala Glu Arg Gln Arg Met
            330                 335                 340

GAG GAG CCG GAT AAT CTG GAG CGG ATG GTC TCG ATC CTC TCG TTT GTT        1169
Glu Glu Pro Asp Asn Leu Glu Arg Met Val Ser Ile Leu Ser Phe Val
345                 350                 355

GCG GTC AGG CTG TTA CAG CTC AGA GAA AGC TTC ACG CCG CCG CAA GCA        1217
Ala Val Arg Leu Leu Gln Leu Arg Glu Ser Phe Thr Pro Pro Gln Ala
360                 365                 370                 375

CTC AGG GCG CAA GGG CTG CTA AAG GAA GCG GAA CAC GTA GAA AGC CAG        1265
Leu Arg Ala Gln Gly Leu Leu Lys Glu Ala Glu His Val Glu Ser Gln
                380                 385                 390

TCC GCA GAA ACG GTG CTG ACC CCG GAT GAA TGT CAG CTA CTG GGC TAT        1313
Ser Ala Glu Thr Val Leu Thr Pro Asp Glu Cys Gln Leu Leu Gly Tyr
                395                 400                 405

CTG GAC AAG GGA AAA CGC AAG CGC AAA GAG AAA GCA GGT AGC TTG CAG        1361
Leu Asp Lys Gly Lys Arg Lys Arg Lys Glu Lys Ala Gly Ser Leu Gln
            410                 415                 420

TGG GCT TAC ATG GCG ATA GCT AGA CTG GGC GGT TTT ATG GAC AGC AAG        1409
Trp Ala Tyr Met Ala Ile Ala Arg Leu Gly Gly Phe Met Asp Ser Lys
        425                 430                 435

CGA ACC GGA ATT GCC AGC TGG GGC GCC CTC TGG GAA GGT TGG GAA GCC        1457
Arg Thr Gly Ile Ala Ser Trp Gly Ala Leu Trp Glu Gly Trp Glu Ala
440                 445                 450                 455

CTG CAA AGT AAA CTG GAT GGC TTT CTT GCC GCC AAG GAT CTG ATG GCG        1505
Leu Gln Ser Lys Leu Asp Gly Phe Leu Ala Ala Lys Asp Leu Met Ala
                    460                 465                 470

CAG GGG ATC AAG ATC TGA TCAAGAGACA G                                   1534
Gln Gly Ile Lys Ile *
            475
```

(2) INFORMATION FOR SEQ ID NO:2:

(i) SEQUENCE CHARACTERISTICS:
        (A) LENGTH: 476 amino acids
        (B) TYPE: amino acid
        (D) TOPOLOGY: linear (ii) MOLECULE TYPE: protein (xi) SEQUENCE DESCRIPTION: SEQ ID NO:2:

```
Met Ile Thr Ser Ala Leu His Arg Ala Ala Asp Trp Ala Lys Ser Val
 1               5                  10                  15

Phe Ser Ser Ala Ala Leu Gly Asp Pro Arg Arg Thr Ala Arg Leu Val
                20                  25                  30

Asn Val Ala Ala Gln Leu Ala Lys Tyr Ser Gly Lys Ser Ile Thr Ile
                35                  40                  45

Ser Ser Glu Gly Ser Lys Ala Ala Gln Glu Gly Ala Tyr Arg Phe Ile
        50                  55                  60

Arg Asn Pro Asn Val Ser Ala Glu Ala Ile Arg Lys Ala Gly Ala Met
 65                  70                  75                  80

Gln Thr Val Lys Leu Ala Gln Glu Phe Pro Glu Leu Leu Ala Ile Glu
                85                  90                  95

Asp Thr Thr Ser Leu Ser Tyr Arg His Gln Val Ala Glu Glu Leu Gly
                100                 105                 110

Lys Leu Gly Ser Ile Gln Asp Lys Ser Arg Gly Trp Trp Val His Ser
                115                 120                 125

Val Leu Leu Glu Ala Thr Thr Phe Arg Thr Val Gly Leu Leu His
130                 135                 140

Gln Glu Trp Trp Met Arg Pro Asp Asp Pro Ala Asp Ala Asp Glu Lys
145                 150                 155                 160

Glu Ser Gly Lys Trp Leu Ala Ala Ala Thr Ser Arg Leu Arg Met
                165                 170                 175

Gly Ser Met Met Ser Asn Val Ile Ala Val Cys Asp Arg Glu Ala Asp
                180                 185                 190

Ile His Ala Tyr Leu Gln Asp Arg Leu Ala His Asn Glu Arg Phe Val
                195                 200                 205

Val Arg Ser Lys His Pro Arg Lys Asp Val Glu Ser Gly Leu Tyr Leu
                210                 215                 220

Ile Asp His Leu Lys Asn Gln Pro Glu Leu Gly Gly Tyr Gln Ile Ser
225                 230                 235                 240

Ile Pro Gln Lys Gly Val Val Asp Lys Arg Gly Lys Arg Lys Asn Arg
                245                 250                 255

Pro Ala Arg Lys Ala Ser Leu Ser Leu Arg Ser Gly Arg Ile Thr Leu
                260                 265                 270

Lys Gln Gly Asn Ile Thr Leu Asn Ala Val Leu Ala Glu Glu Ile Asn
                275                 280                 285

Pro Pro Lys Gly Glu Thr Pro Leu Lys Trp Leu Leu Thr Gly Glu
                290                 295                 300

Pro Val Glu Ser Leu Ala Gln Ala Leu Arg Val Ile Asp Ile Tyr Thr
305                 310                 315                 320

His Arg Trp Arg Ile Glu Glu Phe His Lys Ala Trp Lys Thr Gly Ala
                325                 330                 335

Gly Ala Glu Arg Gln Arg Met Glu Glu Pro Asp Asn Leu Glu Arg Met
                340                 345                 350

Val Ser Ile Leu Ser Phe Val Ala Val Arg Leu Leu Gln Leu Arg Glu
                355                 360                 365

Ser Phe Thr Pro Pro Gln Ala Leu Arg Ala Gln Gly Leu Leu Lys Glu
                370                 375                 380

Ala Glu His Val Glu Ser Gln Ser Ala Glu Thr Val Leu Thr Pro Asp
385                 390                 395                 400
```

```
Glu Cys Gln Leu Leu Gly Tyr Leu Asp Lys Gly Lys Arg Lys Arg Lys
            405                 410                 415

Glu Lys Ala Gly Ser Leu Gln Trp Ala Tyr Met Ala Ile Ala Arg Leu
            420                 425                 430

Gly Gly Phe Met Asp Ser Lys Arg Thr Gly Ile Ala Ser Trp Gly Ala
            435                 440                 445

Leu Trp Glu Gly Trp Glu Ala Leu Gln Ser Lys Leu Asp Gly Phe Leu
450                 455                 460

Ala Ala Lys Asp Leu Met Ala Gln Gly Ile Lys Ile
465             470              475

(2) INFORMATION FOR SEQ ID NO:3:

(i) SEQUENCE CHARACTERISTICS:
        (A) LENGTH: 5838 base pairs
        (B) TYPE: nucleic acid
        (C) STRANDEDNESS: double
        (D) TOPOLOGY: circular (ii) MOLECULE TYPE: other nucleic acid
        (A) DESCRIPTION: /desc = "Plasmid DNA"

(vii) IMMEDIATE SOURCE:
        (B) CLONE: pRZTL1

(ix) FEATURE:
        (A) NAME/KEY: insertion_seq
        (B) LOCATION: 1..19

(ix) FEATURE:
        (A) NAME/KEY: CDS
        (B) LOCATION: 77..1267
        (D) OTHER INFORMATION: /function= "tetracycline
            resistance"

(ix) FEATURE:
        (A) NAME/KEY: CDS
        (B) LOCATION: complement (2301..2960)
        (D) OTHER INFORMATION: /function= "chloramphenicol
            resistance"

(ix) FEATURE:
        (A) NAME/KEY: insertion_seq
        (B) LOCATION: 4564..4582

(ix) FEATURE:
        (A) NAME/KEY: CDS
        (B) LOCATION: 4715..5530
        (D) OTHER INFORMATION: /function= "kanamycin resistance"

(xi) SEQUENCE DESCRIPTION: SEQ ID NO:3:

CTGACTCTTA TACACAAGTA AGCTTTAATG CGGTAGTTTA TCACAGTTAA ATTGCTAACG        60

CAGTCAGGCA CCGTGT ATG AAA TCT AAC AAT GCG CTC ATC GTC ATC CTC          109
                 Met Lys Ser Asn Asn Ala Leu Ile Val Ile Leu
                                480                 485

GGC ACC GTC ACC CTG GAT GCT GTA GGC ATA GGC TTG GTT ATG CCG GTA        157
Gly Thr Val Thr Leu Asp Ala Val Gly Ile Gly Leu Val Met Pro Val
            490                 495                 500

CTG CCG GGC CTC TTG CGG GAT ATC GTC CAT TCC GAC AGC ATC GCC AGT        205
Leu Pro Gly Leu Leu Arg Asp Ile Val His Ser Asp Ser Ile Ala Ser
505                 510                 515                 520

CAC TAT GGC GTG CTG CTA GCG CTA TAT GCG TTG ATG CAA TTT CTA TGC        253
His Tyr Gly Val Leu Leu Ala Leu Tyr Ala Leu Met Gln Phe Leu Cys
                525                 530                 535

GCA CCC GTT CTC GGA GCA CTG TCC GAC CGC TTT GGC CGC CGC CCA GTC        301
Ala Pro Val Leu Gly Ala Leu Ser Asp Arg Phe Gly Arg Arg Pro Val
            540                 545                 550
```

-continued

| | | |
|---|---|---|
| CTG CTC GCT TCG CTA CTT GGA GCC ACT ATC GAC TAC GCG ATC ATG GCG<br>Leu Leu Ala Ser Leu Leu Gly Ala Thr Ile Asp Tyr Ala Ile Met Ala<br>555                          560                         565 | 349 |
| ACC ACA CCC GTC CTG TGG ATC CTC TAC GCC GGA CGC ATC GTG GCC GGC<br>Thr Thr Pro Val Leu Trp Ile Leu Tyr Ala Gly Arg Ile Val Ala Gly<br>570                          575                         580 | 397 |
| ATC ACC GGC GCC ACA GGT GCG GTT GCT GGC GCC TAT ATC GCC GAC ATC<br>Ile Thr Gly Ala Thr Gly Ala Val Ala Gly Ala Tyr Ile Ala Asp Ile<br>585                          590                         595                         600 | 445 |
| ACC GAT GGG GAA GAT CGG GCT CGC CAC TTC GGG CTC ATG AGC GCT TGT<br>Thr Asp Gly Glu Asp Arg Ala Arg His Phe Gly Leu Met Ser Ala Cys<br>                        605                         610                         615 | 493 |
| TTC GGC GTG GGT ATG GTG GCA GGC CCC GTG GCC GGG GGA CTG TTG GGC<br>Phe Gly Val Gly Met Val Ala Gly Pro Val Ala Gly Gly Leu Leu Gly<br>                620                         625                         630 | 541 |
| GCC ATC TCC TTG CAT GCA CCA TTC CTT GCG GCG GCG GTG CTC AAC GGC<br>Ala Ile Ser Leu His Ala Pro Phe Leu Ala Ala Ala Val Leu Asn Gly<br>                635                         640                         645 | 589 |
| CTC AAC CTA CTA CTG GGC TGC TTC CTA ATG CAG GAG TCG CAT AAG GGA<br>Leu Asn Leu Leu Leu Gly Cys Phe Leu Met Gln Glu Ser His Lys Gly<br>650                          655                         660 | 637 |
| GAG CGT CGA CCG ATG CCC TTG AGA GCC TTC AAC CCA GTC AGC TCC TTC<br>Glu Arg Arg Pro Met Pro Leu Arg Ala Phe Asn Pro Val Ser Ser Phe<br>665                          670                         675                         680 | 685 |
| CGG TGG GCG CGG GGC ATG ACT ATC GTC GCC GCA CTT ATG ACT GTC TTC<br>Arg Trp Ala Arg Gly Met Thr Ile Val Ala Ala Leu Met Thr Val Phe<br>                685                         690                         695 | 733 |
| TTT ATC ATG CAA CTC GTA GGA CAG GTG CCG GCA GCG CTC TGG GTC ATT<br>Phe Ile Met Gln Leu Val Gly Gln Val Pro Ala Ala Leu Trp Val Ile<br>                    700                         705                         710 | 781 |
| TTC GGC GAG GAC CGC TTT CGC TGG AGC GCG ACG ATG ATC GGC CTG TCG<br>Phe Gly Glu Asp Arg Phe Arg Trp Ser Ala Thr Met Ile Gly Leu Ser<br>                715                         720                         725 | 829 |
| CTT GCG GTA TTC GGA ATC TTG CAC GCC CTC GCT CAA GCC TTC GTC ACT<br>Leu Ala Val Phe Gly Ile Leu His Ala Leu Ala Gln Ala Phe Val Thr<br>730                          735                         740 | 877 |
| GGT CCC GCC ACC AAA CGT TTC GGC GAG AAG CAG GCC ATT ATC GCC GGC<br>Gly Pro Ala Thr Lys Arg Phe Gly Glu Lys Gln Ala Ile Ile Ala Gly<br>745                          750                         755                         760 | 925 |
| ATG GCG GCC GAC GCG CTG GGC TAC GTC TTG CTG GCG TTC GCG ACG CGA<br>Met Ala Ala Asp Ala Leu Gly Tyr Val Leu Leu Ala Phe Ala Thr Arg<br>                    765                         770                         775 | 973 |
| GGC TGG ATG GCC TTC CCC ATT ATG ATT CTT CTC GCT TCC GGC GGC ATC<br>Gly Trp Met Ala Phe Pro Ile Met Ile Leu Leu Ala Ser Gly Gly Ile<br>                    780                         785                         790 | 1021 |
| GGG ATG CCC GCG TTG CAG GCC ATG CTG TCC AGG CAG GTA GAT GAC GAC<br>Gly Met Pro Ala Leu Gln Ala Met Leu Ser Arg Gln Val Asp Asp Asp<br>                    795                         800                         805 | 1069 |
| CAT CAG GGA CAG CTT CAA GGA TCG CTC GCG GCT CTT ACC AGC CTA ACT<br>His Gln Gly Gln Leu Gln Gly Ser Leu Ala Ala Leu Thr Ser Leu Thr<br>810                          815                         820 | 1117 |
| TCG ATC ACT GGA CCG CTG ATC GTC ACG GCG ATT TAT GCC GCC TCG GCG<br>Ser Ile Thr Gly Pro Leu Ile Val Thr Ala Ile Tyr Ala Ala Ser Ala<br>825                          830                         835                         840 | 1165 |
| AGC ACA TGG AAC GGG TTG GCA TGG ATT GTA GGC GCC GCC CTA TAC CTT<br>Ser Thr Trp Asn Gly Leu Ala Trp Ile Val Gly Ala Ala Leu Tyr Leu<br>                    845                         850                         855 | 1213 |
| GTC TGC CTC CCC GCG TTG CGT CGC GGT GCA TGG AGC CGG GCC ACC TCG<br>Val Cys Leu Pro Ala Leu Arg Arg Gly Ala Trp Ser Arg Ala Thr Ser<br>                    860                         865                         870 | 1261 |

| | |
|---|---|
| ACC TGA ATGGAAGCCG GCGGCACCTC GCTAACGGAT TCACCACTCC AAGAATTGGA<br>Thr  * | 1317 |
| GCCAATCAAT TCTTGCGGAG AACTGTGAAT GCGCAAACCA ACCCTTGGCA GAACATATCC | 1377 |
| ATCGCGTCCG CCATCTCCAG CAGCCGCACG CGGCGCATCT CGGGCAGCGT TGGGTCCTGG | 1437 |
| CCACGGGTGC GCATGATCGT GCTCCTGTCG TTGAGGACCC GGCTAGGCTG GCGGGGTTGC | 1497 |
| CTTACTGGTT AGCAGAATGA ATCACCGATA CGCGAGCGAA CGTGAAGCGA CTGCTGCTGC | 1557 |
| AAAACGTCTG CGACCTGAGC AACAACATGA ATGGTCTTCG GTTTCCGTGT TTCGTAAAGT | 1617 |
| CTGGAAACGC GGAAGTCCCC TACGTGCTGC TGAAGTTGCC CGCAACAGAG AGTGGAACCA | 1677 |
| ACCGGTGATA CCACGATACT ATGACTGAGA GTCAACGCCA TGAGCGGCCT CATTTCTTAT | 1737 |
| TCTGAGTTAC AACAGTCCGC ACCGCTGTCC GGTAGCTCCT TCCGGTGGGC GCGGGGCATG | 1797 |
| ACTATCGTCG CCGCACTTAT GACTGTCTTC TTTATCATGC AACTCGTAGG ACAGGTGCCG | 1857 |
| GCAGCGCCCA ACAGTCCCCC GGCCACGGGG CCTGCCACCA TACCCACGCC GAAACAAGCG | 1917 |
| CCCTGCACCA TTATGTTCCG GATCTGCATC GCAGGATGCT GCTGGCTACC CTGTGGAACA | 1977 |
| CCTACATCTG TATTAACGAA GCGCTAACCG TTTTTATCAG GCTCTGGGAG GCAGAATAAA | 2037 |
| TGATCATATC GTCAATTATT ACCTCCACGG GGAGAGCCTG AGCAAACTGG CCTCAGGCAT | 2097 |
| TTGAGAAGCA CACGGTCACA CTGCTTCCGG TAGTCAATAA ACCGGTAAAC CAGCAATAGA | 2157 |
| CATAAGCGGC TATTTAACGA CCCTGCCCTG AACCGACGAC CGGGTCGAAT TGCTTTCGA | 2217 |
| ATTTCTGCCA TTCATCCGCT TATTATCAAT TATTCAGGCG TAGCACCAGG CGTTTAAGGG | 2277 |
| CACCAATAAC TGCCTTAAAA AAATTACGCC CCGCCCTGCC ACTCATCGCA GTACTGTTGT | 2337 |
| AATTCATTAA GCATTCTGCC GACATGGAAG CCATCACAGA CGGCATGATG AACCTGAATC | 2397 |
| GCCAGCGGCA TCAGCACCTT GTCGCCTTGC GTATAATATT TGCCCATGGT GAAAACGGGG | 2457 |
| GCGAAGAAGT TGTCCATATT GGCCACGTTT AAATCAAAAC TGGTGAAACT CACCCAGGGA | 2517 |
| TTGGCTGAGA CGAAAAACAT ATTCTCAATA AACCCTTTAG GGAAATAGGC CAGGTTTTCA | 2577 |
| CCGTAACACG CCACATCTTG CGAATATATG TGTAGAAACT GCCGGAAATC GTCGTGGTAT | 2637 |
| TCACTCCAGA GCGATGAAAA CGTTTCAGTT TGCTCATGGA AAACGGTGTA ACAAGGGTGA | 2697 |
| ACACTATCCC ATATCACCAG CTCACCGTCT TCATTGCCA TACGGAATTC CGGATGAGCA | 2757 |
| TTCATCAGGC GGGCAAGAAT GTGAATAAAG GCCGGATAAA ACTTGTGCTT ATTTTTCTTT | 2817 |
| ACGGTCTTTA AAAGGCCGT AATATCCAGC TGAACGGTCT GGTTATAGGT ACATTGAGCA | 2877 |
| ACTGACTGAA ATGCCTCAAA ATGTTCTTTA CGATGCCATT GGGATATATC AACGGTGGTA | 2937 |
| TATCCAGTGA TTTTTTTCTC CATTTTAGCT TCCTTAGCTC CTGAAAATCT CGATAACTCA | 2997 |
| AAAAATACGC CCGGTAGTGA TCTTATTTCA TTATGGTGAA AGTTGGAACC TCTTACGTGC | 3057 |
| CGATCAACGT CTCATTTTCG CCAAAAGTTG GCCCAGGGCT TCCCGGTATC AACAGGGACA | 3117 |
| CCAGGATTTA TTTATTCTGC GAAGTGATCT TCCGTCACAG GTATTATTC GGCGCAAAGT | 3177 |
| GCGTCGGGTG ATGCTGCCAA CTTACTGATT TAGTGTATGA TGGTGTTTTT GAGGTGCTCC | 3237 |
| AGTGGCTTCT GTTTCTATCA GCTGTCCCTC CTGTTCAGCT ACTGACGGG TGGTGCGTAA | 3297 |
| CGGCAAAAGC ACCGCCGGAC ATCAGCGCTA GCGGAGTGTA TACTGGCTTA CTATGTTGGC | 3357 |
| ACTGATGAGG GTGTCAGTGA AGTGCTTCAT GTGGCAGGAG AAAAAAGGCT GCACCGGTGC | 3417 |
| GTCAGCAGAA TATGTGATAC AGGATATATT CCGCTTCCTC GCTCACTGAC TCGCTACGCT | 3477 |
| CGGTCGTTCG ACTGCGGCGA GCGGAAATGG CTTACGAACG GGGCGGAGAT TTCCTGGAAG | 3537 |
| ATGCCAGGAA GATACTTAAC AGGGAAGTGA GAGGGCCGCG GCAAAGCCGT TTTTCCATAG | 3597 |
| GCTCCGCCCC CCTGACAAGC ATCACGAAAT CTGACGCTCA AATCAGTGGT GGCGAAACCC | 3657 |

```
GACAGGACTA TAAAGATACC AGGCGTTTCC CCTGGCGGCT CCCTCGTGCG CTCTCCTGTT    3717

CCTGCCTTTC GGTTTACCGG TGTCATTCCG CTGTTATGGC CGCGTTTGTC TCATTCCACG    3777

CCTGACACTC AGTTCCGGGT AGGCAGTTCG CTCCAAGCTG GACTGTATGC ACGAACCCCC    3837

CGTTCAGTCC GACCGCTGCG CCTTATCCGG TAACTATCGT CTTGAGTCCA ACCCGGAAAG    3897

ACATGCAAAA GCACCACTGG CAGCAGCCAC TGGTAATTGA TTTAGAGGAG TTAGTCTTGA    3957

AGTCATGCGC CGGTTAAGGC TAAACTGAAA GGACAAGTTT TGGTGACTGC GCTCCTCCAA    4017

GCCAGTTACC TCGGTTCAAA GAGTTGGTAG CTCAGAGAAC CTTCGAAAAA CCGCCCTGCA    4077

AGGCGGTTTT TTCGTTTTCA GAGCAAGAGA TTACGCGCAG ACCAAAACGA TCTCAAGAAG    4137

ATCATCTTAT TAATCAGATA AAATATTTCT AGAGGTGAAC CATCACCCTA ATCAAGTTTT    4197

TTGGGGTCGA GGTGCCGTAA AGCACTAAAT CGGAACCCTA AAGGGATGCC CCGATTTAGA    4257

GCTTGACGGG GAAAGCCGGC GAACGTGGCG AGAAAGGAAG GAAGAAAGC GAAAGGAGCG     4317

GGCGCTAGGG CGCTGGCAAG TGTAGCGGTC ACGCTGCGCG TAACCACCAC ACCCGCCGCG    4377

CTTAATGCGC CGCTACAGCG CCATTCGCCA TTCAGGCTGC GCAACTGTTG GAAGGGCGA     4437

TCGGTGCGGG CCTCTTCGCT ATTACGCCAG CTGGCGAAAG GGGGATGTGC TGCAAGGCGA    4497

TTAAGTTGGG TAACGCCAGG GTTTTCCCAG TCACGACGTT GTAAAACGAC GGCCAGTGCC    4557

AAGCTTACTT GTGTATAAGA GTCAGTCGAC CTGCAGGGGG GGGGGGAAA GCCACGTTGT     4617

GTCTCAAAAT CTCTGATGTT ACATTGCACA AGATAAAAAT ATATCATCAT GAACAATAAA    4677

ACTGTCTGCT TACATAAACA GTAATACAAG GGGTGTT ATG AGC CAT ATT CAA CGG    4732
                                        Met Ser His Ile Gln Arg
                                          1               5

GAA ACG TCT TGC TCG AGG CCG CGA TTA AAT TCC AAC ATG GAT GCT GAT    4780
Glu Thr Ser Cys Ser Arg Pro Arg Leu Asn Ser Asn Met Asp Ala Asp
             10                  15                  20

TTA TAT GGG TAT AAA TGG GCT CGC GAT AAT GTC GGG CAA TCA GGT GCG    4828
Leu Tyr Gly Tyr Lys Trp Ala Arg Asp Asn Val Gly Gln Ser Gly Ala
         25                  30                  35

ACA ATC TAT CGA TTG TAT GGG AAG CCC GAT GCG CCA GAG TTG TTT CTG    4876
Thr Ile Tyr Arg Leu Tyr Gly Lys Pro Asp Ala Pro Glu Leu Phe Leu
     40                  45                  50

AAA CAT GGC AAA GGT AGC GTT GCC AAT GAT GTT ACA GAT GAG ATG GTC    4924
Lys His Gly Lys Gly Ser Val Ala Asn Asp Val Thr Asp Glu Met Val
 55                  60                  65                  70

AGA CTA AAC TGG CTG ACG GAA TTT ATG CCT CTT CCG ACC ATC AAG CAT    4972
Arg Leu Asn Trp Leu Thr Glu Phe Met Pro Leu Pro Thr Ile Lys His
                 75                  80                  85

TTT ATC CGT ACT CCT GAT GAT GCA TGG TTA CTC ACC ACT GCG ATC CCC    5020
Phe Ile Arg Thr Pro Asp Asp Ala Trp Leu Leu Thr Thr Ala Ile Pro
             90                  95                 100

GGG AAA ACA GCA TTC CAG GTA TTA GAA GAA TAT CCT GAT TCA GGT GAA    5068
Gly Lys Thr Ala Phe Gln Val Leu Glu Glu Tyr Pro Asp Ser Gly Glu
        105                 110                 115

AAT ATT GTT GAT GCG CTG GCA GTG TTC CTG CGC CGG TTG CAT TCG ATT    5116
Asn Ile Val Asp Ala Leu Ala Val Phe Leu Arg Arg Leu His Ser Ile
    120                 125                 130

CCT GTT TGT AAT TGT CCT TTT AAC AGC GAT CGC GTA TTT CGT CTC GCT    5164
Pro Val Cys Asn Cys Pro Phe Asn Ser Asp Arg Val Phe Arg Leu Ala
135                 140                 145                 150

CAG GCG CAA TCA CGA ATG AAT AAC GGT TTG GTT GAT GCG AGT GAT TTT    5212
Gln Ala Gln Ser Arg Met Asn Asn Gly Leu Val Asp Ala Ser Asp Phe
                155                 160                 165
```

| | | | | | | | | | | | | | | | |
|---|---|---|---|---|---|---|---|---|---|---|---|---|---|---|---|
| GAT | GAC | GAG | CGT | AAT | GGC | TGG | CCT | GTT | GAA | CAA | GTC | TGG | AAA | GAA | ATG | 5260 |
| Asp | Asp | Glu | Arg | Asn | Gly | Trp | Pro | Val | Glu | Gln | Val | Trp | Lys | Glu | Met |
| | | 170 | | | | | 175 | | | | | 180 | | | |
| CAT | AAG | CTT | TTG | CCA | TTC | TCA | CCG | GAT | TCA | GTC | GTC | ACT | CAT | GGT | GAT | 5308 |
| His | Lys | Leu | Leu | Pro | Phe | Ser | Pro | Asp | Ser | Val | Val | Thr | His | Gly | Asp |
| | | | 185 | | | | | 190 | | | | | 195 | | |
| TTC | TCA | CTT | GAT | AAC | CTT | ATT | TTT | GAC | GAG | GGG | AAA | TTA | ATA | GGT | TGT | 5356 |
| Phe | Ser | Leu | Asp | Asn | Leu | Ile | Phe | Asp | Glu | Gly | Lys | Leu | Ile | Gly | Cys |
| | | 200 | | | | | 205 | | | | | 210 | | | |
| ATT | GAT | GTT | GGA | CGA | GTC | GGA | ATC | GCA | GAC | CGA | TAC | CAG | GAT | CTT | GCC | 5404 |
| Ile | Asp | Val | Gly | Arg | Val | Gly | Ile | Ala | Asp | Arg | Tyr | Gln | Asp | Leu | Ala |
| 215 | | | | 220 | | | | | 225 | | | | | 230 | |
| ATC | CTA | TGG | AAC | TGC | CTC | GGT | GAG | TTT | TCT | CCT | TCA | TTA | CAG | AAA | CGG | 5452 |
| Ile | Leu | Trp | Asn | Cys | Leu | Gly | Glu | Phe | Ser | Pro | Ser | Leu | Gln | Lys | Arg |
| | | | | 235 | | | | | 240 | | | | | 245 | |
| CTT | TTT | CAA | AAA | TAT | GGT | ATT | GAT | AAT | CCT | GAT | ATG | AAT | AAA | TTG | CAG | 5500 |
| Leu | Phe | Gln | Lys | Tyr | Gly | Ile | Asp | Asn | Pro | Asp | Met | Asn | Lys | Leu | Gln |
| | | | 250 | | | | | 255 | | | | | 260 | | |

| | | | | | | | | |
|---|---|---|---|---|---|---|---|---|
| TTT | CAT | TTG | ATG | CTC | GAT | GAG | TTT | TTC | TAA | TCAGAATTGG TTAATTGGTT | 5550 |
| Phe | His | Leu | Met | Leu | Asp | Glu | Phe | Phe | * |
| | | | 265 | | | | | 270 |

GTAACACTGG CAGAGCATTA CGCTGACTTG ACGGGACGGC GGCTTTGTTG AATAAATCGA    5610

ACTTTTGCTG AGTTGAAGGA TCAGATCACG CATCTTCCCG ACAACGCAGA CCGTTCCGTG    5670

GCAAAGCAAA AGTTCAAAAT CACCAACTGG TCCACCTACA ACAAAGCTCT CATCAACCGT    5730

GGCTCCCTCA CTTTCTGGCT GGATGATGGG GCGATTCAGG CCTGGTATGA GTCAGCAACA    5790

CCTTCTTCAC GAGGCAGACC TCAGCGCCCC CCCCCCCCTG CAGGTCGA    5838

(2) INFORMATION FOR SEQ ID NO:4:

(i) SEQUENCE CHARACTERISTICS:
        (A) LENGTH: 396 amino acids
        (B) TYPE: amino acid
        (D) TOPOLOGY: linear (ii) MOLECULE TYPE: protein (xi) SEQUENCE DESCRIPTION: SEQ ID NO:4:

| | | | | | | | | | | | | | | |
|---|---|---|---|---|---|---|---|---|---|---|---|---|---|---|
| Met | Lys | Ser | Asn | Asn | Ala | Leu | Ile | Val | Ile | Leu | Gly | Thr | Val | Thr | Leu |
| 1 | | | | 5 | | | | | 10 | | | | | 15 | |
| Asp | Ala | Val | Gly | Ile | Gly | Leu | Val | Met | Pro | Val | Leu | Pro | Gly | Leu | Leu |
| | | | 20 | | | | | 25 | | | | | 30 | | |
| Arg | Asp | Ile | Val | His | Ser | Asp | Ser | Ile | Ala | Ser | His | Tyr | Gly | Val | Leu |
| | | | 35 | | | | | 40 | | | | | 45 | | |
| Leu | Ala | Leu | Tyr | Ala | Leu | Met | Gln | Phe | Leu | Cys | Ala | Pro | Val | Leu | Gly |
| | 50 | | | | | 55 | | | | | 60 | | | | |
| Ala | Leu | Ser | Asp | Arg | Phe | Gly | Arg | Arg | Pro | Val | Leu | Leu | Ala | Ser | Leu |
| 65 | | | | | 70 | | | | | 75 | | | | | 80 |
| Leu | Gly | Ala | Thr | Ile | Asp | Tyr | Ala | Ile | Met | Ala | Thr | Thr | Pro | Val | Leu |
| | | | | 85 | | | | | 90 | | | | | 95 | |
| Trp | Ile | Leu | Tyr | Ala | Gly | Arg | Ile | Val | Ala | Gly | Ile | Thr | Gly | Ala | Thr |
| | | | 100 | | | | | 105 | | | | | 110 | | |
| Gly | Ala | Val | Ala | Gly | Ala | Tyr | Ile | Ala | Asp | Ile | Thr | Asp | Gly | Glu | Asp |
| | | | 115 | | | | | 120 | | | | | 125 | | |
| Arg | Ala | Arg | His | Phe | Gly | Leu | Met | Ser | Ala | Cys | Phe | Gly | Val | Gly | Met |
| | 130 | | | | | 135 | | | | | 140 | | | | |
| Val | Ala | Gly | Pro | Val | Ala | Gly | Gly | Leu | Leu | Gly | Ala | Ile | Ser | Leu | His |
| 145 | | | | | 150 | | | | | 155 | | | | | 160 |

```
Ala Pro Phe Leu Ala Ala Val Leu Asn Gly Leu Asn Leu Leu
            165                 170                 175

Gly Cys Phe Leu Met Gln Glu Ser His Lys Gly Glu Arg Arg Pro Met
            180                 185                 190

Pro Leu Arg Ala Phe Asn Pro Val Ser Ser Phe Arg Trp Ala Arg Gly
            195                 200                 205

Met Thr Ile Val Ala Ala Leu Met Thr Val Phe Phe Ile Met Gln Leu
        210                 215                 220

Val Gly Gln Val Pro Ala Ala Leu Trp Val Ile Phe Gly Glu Asp Arg
225                 230                 235                 240

Phe Arg Trp Ser Ala Thr Met Ile Gly Leu Ser Leu Ala Val Phe Gly
                245                 250                 255

Ile Leu His Ala Leu Ala Gln Ala Phe Val Thr Gly Pro Ala Thr Lys
                260                 265                 270

Arg Phe Gly Glu Lys Gln Ala Ile Ile Ala Gly Met Ala Ala Asp Ala
            275                 280                 285

Leu Gly Tyr Val Leu Leu Ala Phe Ala Thr Arg Gly Trp Met Ala Phe
        290                 295                 300

Pro Ile Met Ile Leu Leu Ala Ser Gly Gly Ile Gly Met Pro Ala Leu
305                 310                 315                 320

Gln Ala Met Leu Ser Arg Gln Val Asp Asp His Gln Gly Gln Leu
                325                 330                 335

Gln Gly Ser Leu Ala Ala Leu Thr Ser Leu Thr Ser Ile Thr Gly Pro
            340                 345                 350

Leu Ile Val Thr Ala Ile Tyr Ala Ala Ser Ala Ser Thr Trp Asn Gly
                355                 360                 365

Leu Ala Trp Ile Val Gly Ala Ala Leu Tyr Leu Val Cys Leu Pro Ala
        370                 375                 380

Leu Arg Arg Gly Ala Trp Ser Arg Ala Thr Ser Thr
385                 390                 395
```

(2) INFORMATION FOR SEQ ID NO:5:

(i) SEQUENCE CHARACTERISTICS:
        (A) LENGTH: 219 amino acids
        (B) TYPE: amino acid
        (D) TOPOLOGY: linear (ii) MOLECULE TYPE: protein (xi) SEQUENCE DESCRIPTION: SEQ ID NO:5:

```
Met Glu Lys Lys Ile Thr Gly Tyr Thr Thr Val Asp Ile Ser Gln Trp
1               5                   10                  15

His Arg Lys Glu His Phe Glu Ala Phe Gln Ser Val Ala Gln Cys Thr
            20                  25                  30

Tyr Asn Gln Thr Val Gln Leu Asp Ile Thr Ala Phe Leu Lys Thr Val
        35                  40                  45

Lys Lys Asn Lys His Lys Phe Tyr Pro Ala Phe Ile His Ile Leu Ala
    50                  55                  60

Arg Leu Met Asn Ala His Pro Glu Phe Arg Met Ala Met Lys Asp Gly
65              70                  75                  80

Glu Leu Val Ile Trp Asp Ser Val His Pro Cys Tyr Thr Val Phe His
                85                  90                  95

Glu Gln Thr Glu Thr Phe Ser Ser Leu Trp Ser Glu Tyr His Asp Asp
            100                 105                 110

Phe Arg Gln Phe Leu His Ile Tyr Ser Gln Asp Val Ala Cys Tyr Gly
        115                 120                 125
```

```
Glu Asn Leu Ala Tyr Phe Pro Lys Gly Phe Ile Glu Asn Met Phe Phe
            130                 135                 140

Val Ser Ala Asn Pro Trp Val Ser Phe Thr Ser Phe Asp Leu Asn Val
145                 150                 155                 160

Ala Asn Met Asp Asn Phe Phe Ala Pro Val Phe Thr Met Gly Lys Tyr
                165                 170                 175

Tyr Thr Gln Gly Asp Lys Val Leu Met Pro Leu Ala Ile Gln Val His
            180                 185                 190

His Ala Val Cys Asp Gly Phe His Val Gly Arg Met Leu Asn Glu Leu
            195                 200                 205

Gln Gln Tyr Cys Asp Glu Trp Gln Gly Gly Ala
            210                 215                 220

(2) INFORMATION FOR SEQ ID NO:6:

(i) SEQUENCE CHARACTERISTICS:
        (A) LENGTH:  271 amino acids
        (B) TYPE: amino acid
        (D) TOPOLOGY: linear (ii) MOLECULE TYPE: protein (xi) SEQUENCE DESCRIPTION: SEQ ID NO:6:

Met Ser His Ile Gln Arg Glu Thr Ser Cys Ser Arg Pro Arg Leu Asn
  1               5                  10                  15

Ser Asn Met Asp Ala Asp Leu Tyr Gly Tyr Lys Trp Ala Arg Asp Asn
                 20                  25                  30

Val Gly Gln Ser Gly Ala Thr Ile Tyr Arg Leu Tyr Gly Lys Pro Asp
             35                  40                  45

Ala Pro Glu Leu Phe Leu Lys His Gly Lys Gly Ser Val Ala Asn Asp
         50                  55                  60

Val Thr Asp Glu Met Val Arg Leu Asn Trp Leu Thr Glu Phe Met Pro
 65                  70                  75                  80

Leu Pro Thr Ile Lys His Phe Ile Arg Thr Pro Asp Asp Ala Trp Leu
                 85                  90                  95

Leu Thr Thr Ala Ile Pro Gly Lys Thr Ala Phe Gln Val Leu Glu Glu
                100                 105                 110

Tyr Pro Asp Ser Gly Glu Asn Ile Val Asp Ala Leu Ala Val Phe Leu
            115                 120                 125

Arg Arg Leu His Ser Ile Pro Val Cys Asn Cys Pro Phe Asn Ser Asp
130                 135                 140

Arg Val Phe Arg Leu Ala Gln Ala Gln Ser Arg Met Asn Asn Gly Leu
145                 150                 155                 160

Val Asp Ala Ser Asp Phe Asp Asp Glu Arg Asn Gly Trp Pro Val Glu
                165                 170                 175

Gln Val Trp Lys Glu Met His Lys Leu Leu Pro Phe Ser Pro Asp Ser
            180                 185                 190

Val Val Thr His Gly Asp Phe Ser Leu Asp Asn Leu Ile Phe Asp Glu
            195                 200                 205

Gly Lys Leu Ile Gly Cys Ile Asp Val Gly Arg Val Gly Ile Ala Asp
            210                 215                 220

Arg Tyr Gln Asp Leu Ala Ile Leu Trp Asn Cys Leu Gly Glu Phe Ser
225                 230                 235                 240
```

-continued

```
Pro Ser Leu Gln Lys Arg Leu Phe Gln Lys Tyr Gly Ile Asp Asn Pro
                245                 250                 255

Asp Met Asn Lys Leu Gln Phe His Leu Met Leu Asp Glu Phe Phe
                260                 265             270
```

SYSTEM FOR IN VITRO TRANSPOSITION

STATEMENT REGARDING FEDERALLY SPONSORED RESEARCH OR DEVELOPMENT

This invention was made with United States government support awarded by the following agencies: NIH Grant No.: CM50692. The United States has certain rights in this invention.

FIELD OF THE INVENTION

The present invention relates generally to the field of transposable nucleic acid and, more particularly to production and use of a modified transposase enzyme in a system for introducing genetic changes to nucleic acid.

BACKGROUND OF THE INVENTION

Transposable genetic elements are DNA sequences, found in a wide variety of prokaryotic and eukaryotic organisms, that can move or transpose from one position to another position in a genome. In vivo, intra-chromosomal transpositions as well as transpositions between chromosomal and non-chromosomal genetic material are known. In several systems, transposition is known to be under the control of a transposase enzyme that is typically encoded by the transposable element. The genetic structures and transposition mechanisms of various transposable elements are summarized, for example, in "Transposable Genetic Elements" in "The Encyclopedia of Molecular Biology," Kendrew and Lawrence, Eds., Blackwell Science, Ltd., Oxford (1994), incorporated herein by reference.

In vitro transposition systems that utilize the particular transposable elements of bacteriophage Mu and bacterial transposon Tn10 have been described, by the research groups of Kiyoshi Mizuuchi and Nancy Kleckner, respectively.

The bacteriophage Mu system was first described by Mizuuchi, K., "In Vitro Transposition of Bacteria Phage Mu: A Biochemical Approach to a Novel Replication Reaction," *Cell:*785–794 (1983) and Craigie, R. et al., "A Defined System for the DNA Strand-Transfer Reaction at the Initiation of Bacteriophage Mu Transposition: Protein and DNA Substrate Requirements," *P.N.A.S. U.S.A.* 82:7570–7574 (1985). The DNA donor substrate (mini-Mu) for Mu in vitro reaction normally requires six Mu transposase binding sites (three of about 30 bp at each end) and an enhancer sequence located about 1 kb from the left end. The donor plasmid must be supercoiled. Proteins required are Mu-encoded A and B proteins and host-encoded HU and IHF proteins. Lavoie, B. D, and G. Chaconas, "Transposition of phage Mu DNA," *Curr. Topics Microbiol. Immunol.* 204:83–99 (1995). The Mu-based system is disfavored for in vitro transposition system applications because the Mu termini are complex and sophisticated and because transposition requires additional proteins above and beyond the transposase.

The Tn10 system was described by Morisato, D. and N. Kleckner, "Tn10 Transposition and Circle Formation in vitro," *Cell* 51:101–111 (1987) and by Benjamin, H. W. and N. Kleckner, "Excision Of Tn10 from the Donor Site During Transposition Occurs By Flush Double-Strand Cleavages at the Transposon Termini," *P.N.A.S. U.S.A.* 89:4648–4652 (1992). The Tn10 system involves the a supercoiled circular DNA molecule carrying the transposable element (or a linear DNA molecule plus *E. coli* IHF protein). The transposable element is defined by complex 42 bp terminal sequences with IHF binding site adjacent to the inverted repeat. In fact, even longer (81 bp) ends of Tn10 were used in reported experiments. Sakai, J. et al., "Identification and Characterization of Pre-Cleavage Synaptic Complex that is an Early Intermediate in Tn10 transposition," *E.M.B.O. J.* 14:4374–4383 (1995). In the Tn10 system, chemical treatment of the transposase protein is essential to support active transposition. In addition, the termini of the Tn10 element limit its utility in a generalized in vitro transposition system.

Both the Mu- and Tn10-based in vitro transposition systems are further limited in that they are active only on covalently closed circular, supercoiled DNA targets. What is desired is a more broadly applicable in vitro transposition system that utilizes shorter, more well defined termini and which is active on target DNA of any structure (linear, relaxed circular, and supercoiled circular DNA).

SUMMARY OF THE INVENTION

The present invention is summarized in that an in vitro transposition system comprises a preparation of a suitably modified transposase of bacterial transposon Tn5, a donor DNA molecule that includes a transposable element, a target DNA molecule into which the transposable element can transpose, all provided in a suitable reaction buffer.

The transposable element of the donor DNA molecule is characterized as a transposable DNA sequence of interest, the DNA sequence of interest being flanked at its 5'-and 3'-ends by short repeat sequences that are acted upon in trans by Tn5 transposase.

The invention is further summarized in that the suitably modified transposase enzyme comprises two classes of differences from wild type Tn5 transposase, where each class has a separate measurable effect upon the overall transposition activity of the enzyme and where a greater effect is observed when both modifications are present. The suitably modified enzyme both (1) binds to the repeat sequences of the donor DNA with greater avidity than wild type Tn5 transposase ("class (1) mutation") and (2) is less likely than the wild type protein to assume an inactive multimeric form ("class (2) mutation"). A suitably modified Tn5 transposase of the present invention that contains both class (1) and class (2) modifications induces at least about 100-fold (±10%) more transposition than the wild type enzyme, when tested in combination in an in vivo conjugation assay as described by Weinreich, M. D., "Evidence that the cis Preference of the Tn5 Transposase is Caused by Nonproductive Multimerization," *Genes and Development* 8:2363–2374 (1994), incorporated herein by reference. Under optimal conditions, transposition using the modified transposase may be higher. A modified transposase containing only a class (1) mutation binds to the repeat sequences with sufficiently greater avidity than the wild type Tn5 transposase that such a Tn5 transposase induces about 5- to 50-fold more transposition than the wild type enzyme, when measured in vivo. A modified transposase containing only a class (2) mutation is sufficiently less likely than the wild type Tn5 transposase to assume the multimeric form that such a Tn5 transposase also induces about 5- to 50-fold more transposition than the wild type enzyme, when measured in vivo.

In another aspect, the invention is summarized in that a method for transposing the transposable element from the donor DNA into the target DNA in vitro includes the steps of mixing together the suitably modified Tn5 transposase protein, the donor DNA, and the target DNA in a suitable reaction buffer, allowing the enzyme to bind to the flanking repeat sequences of the donor DNA at a temperature greater than 0° C., but no higher than about 28° C., and then raising the temperature to physiological temperature (about 37° C.) whereupon cleavage and strand transfer can occur.

It is an object of the present invention to provide a useful in vitro transposition system having few structural requirements and high efficiency.

It is another object of the present invention to provide a method that can be broadly applied in various ways, such as to create absolute defective mutants, to provide selective markers to target DNA, to provide portable regions of homology to a target DNA, to facilitate insertion of specialized DNA sequences into target DNA, to provide primer binding sites or tags for DNA sequencing, to facilitate production of genetic fusions for gene expression studies and protein domain mapping, as well as to bring together other desired combinations of DNA sequences (combinatorial genetics).

It is a feature of the present invention that the modified transposase enzyme binds more tightly to DNA than does wild type Tn5 transposase.

It is an advantage of the present invention that the modified transposase facilitates in vitro transposition reaction rates of at least about 100-fold higher than can be achieved using wild type transposase (as measured in vivo). It is noted that the wild-type Tn5 transposase shows no detectable in vitro activity in the system of the present invention. Thus, while it is difficult to calculate an upper limit to the increase in activity, it is clear that hundreds, if not thousands, of colonies are observed when the products of in vitro transposition are assayed in vivo.

It is another advantage of the present invention that in vitro transposition using this system can utilize donor DNA and target DNA that is circular or linear.

It is yet another advantage of the present invention that in vitro transposition using this system requires no outside high energy source and no other protein other than the modified transposase.

Other objects, features, and advantages of the present invention will become apparent upon consideration of the following detailed description.

DETAILED DESCRIPTION OF THE INVENTION

Figure 1:
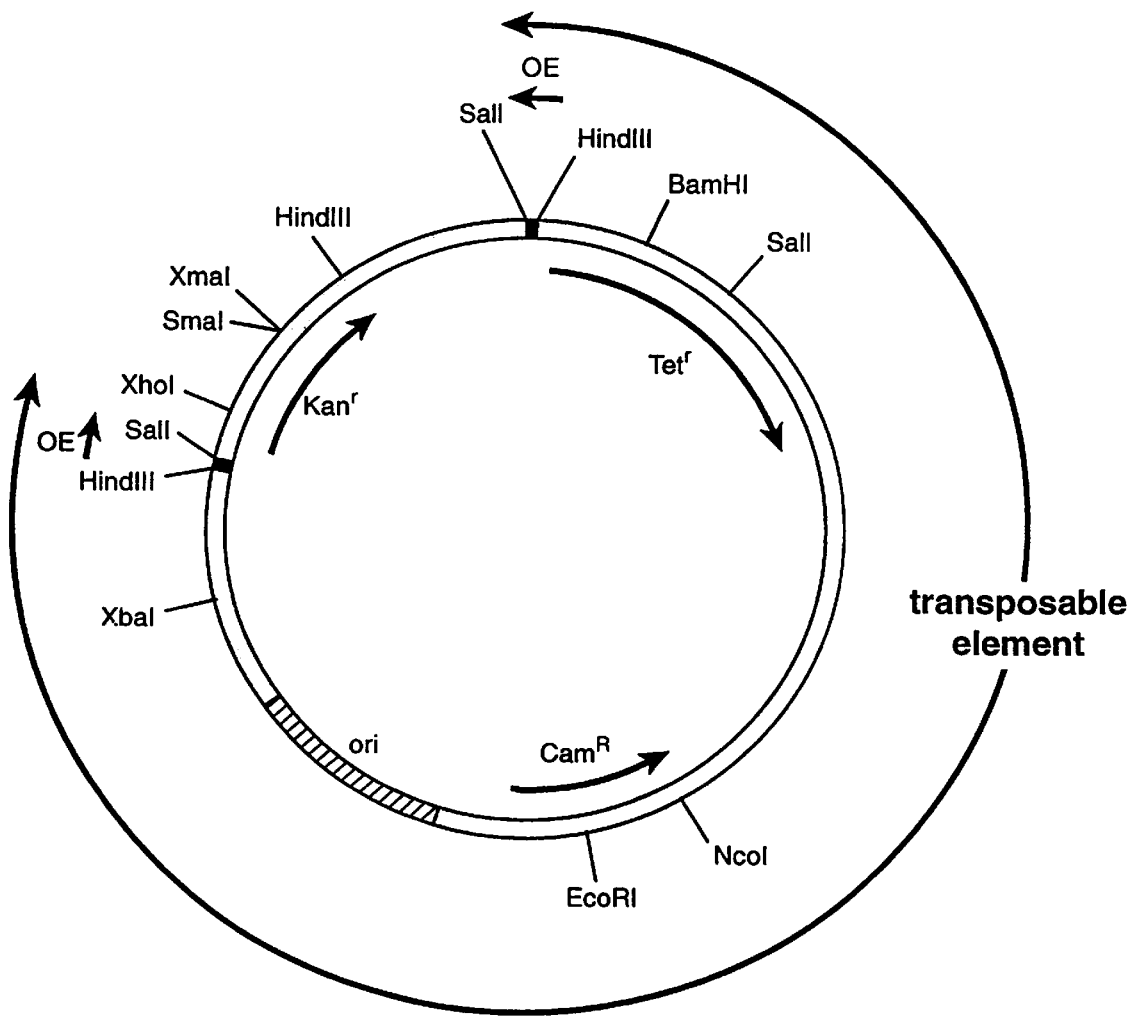
FIG. 1 depicts test plasmid pRZTL1, used herein to demonstrate transposition in vitro of a transposable element located between a pair of Tn5 outside end termini. Plasmid PRZTL1 is also shown and described in SEQ ID NO:3.

It will be appreciated that this technique provides a simple, in vitro system for introducing any transposable element from a donor DNA into a target DNA. It is generally accepted and understood that Tn5 transposition requires only a pair of OE termini, located to either side of the transposable element. These OE termini are generally thought to be 18 or 19 bases in length and are inverted repeats relative to one another. Johnson, R. C., and W. S. Reznikoff, Nature 304:280 (1983), incorporated herein by reference. The Tn5 inverted repeat sequences, which are referred to as "termini" even though they need not be at the termini of the donor DNA molecule, are well known and understood.

Apart from the need to flank the desired transposable element with standard Tn5 outside end ("OE") termini, few other requirements on either the donor DNA or the target DNA are envisioned. It is thought that Tn5 has few, if any, preferences for insertion sites, so it is possible to use the system to introduce desired sequences at random into target DNA. Therefore, it is believed that this method, employing the modified transposase described herein and a simple donor DNA, is broadly applicable to introduce changes into any target DNA, without regard to its nucleotide sequence. It will, thus, be applied to many problems of interest to those skilled in the art of molecular biology.

In the method, the modified transposase protein is combined in a suitable reaction buffer with the donor DNA and the target DNA. A suitable reaction buffer permits the transposition reaction to occur. A preferred, but not necessarily optimized, buffer contains spermidine to condense the DNA, glutamate, and magnesium, as well as a detergent, which is preferably 3-[(3-cholamidopropyl) dimethyl-ammonio]-1-propane sulfonate ("CHAPS"). The mixture can be incubated at a temperature greater than 0° C. and as high as about 28° C. to facilitate binding of the enzyme to the OE termini. Under the buffer conditions used by the inventors in the Examples, a pretreatment temperature of 30° C. was not adequate. A preferred temperature range is between 16° C. and 28° C. A most preferred pretreatment temperature is about 20° C. Under different buffer conditions, however, it may be possible to use other below-physiological temperatures for the binding step. After a short pretreatment period of time (which has not been optimized, but which may be as little as 30 minutes or as much as 2 hours, and is typically 1 hour), the reaction mixture is diluted with 2 volumes of a suitable reaction buffer and shifted to physiological conditions for several more hours (say 2–3 hours) to permit cleavage and strand transfer to occur. A temperature of 37° C., or thereabouts, is adequate. After about 3 hours, the rate of transposition decreases markedly. The reaction can be stopped by phenol-chloroform extraction and can then be desalted by ethanol precipitation.

Following the reaction and subsequent extraction steps, transposition can be assayed by introducing the nucleic acid reaction products into suitable bacterial host cells (e.g., E. coli K-12 DH5α cells (recA⁻); commercially available from Life Technologies (Gibco-BRL)) preferably by electroporation, described by Dower et al., Nuc. Acids. Res. 16:6127 (1988), and monitoring for evidence of transposition, as is described elsewhere herein.

Those persons skilled in the art will appreciate that apart from the changes noted herein, the transposition reaction can proceed under much the same conditions as would be found in an in vivo reaction. Yet, the modified transposase described herein so increases the level of transposition activity that it is now possible to carry out this reaction in vitro where this has not previously been possible. The rates of reaction are even greater when the modified transposase is coupled with an optimized buffer and temperature conditions noted herein.

In another aspect, the present invention is a preparation of a modified Tn5 transposase enzyme that differs from wild type Tn5 transposase in that it (1) binds to the repeat sequences of the donor DNA with greater avidity than wild type Tn5 transposase and (2) is less likely than the wild type protein to assume an inactive multimeric form. An enzyme having these requirements can be obtained from a bacterial host cell containing an expressible gene for the modified enzyme that is under the control of a promoter active in the host cell. Genetic material that encodes the modified Tn5 transposase can be introduced (e.g., by electroporation) into suitable bacterial host cells capable of supporting expression of the genetic material. Known methods for overproducing and preparing other Tn5 transposase mutants are suitably employed. For example, Weinreich, M. D., et al., supra, describes a suitable method for overproducing a Tn5 transposase. A second method for purifying Tn5 transposase was described in de la Cruz, N. B., et al., "Characterization of the Tn5 Transposase and Inhibitor Proteins: A Model for the Inhibition of Transposition," *J. Bact.* 175:6932–6938 (1993), also incorporated herein by reference. It is noted that induction can be carried out at temperatures below 37° C., which is the temperature used by de la Cruz, et al. Temperatures at least in the range of 33 to 37° C. are suitable. The inventors have determined that the method for preparing the modified transposase of the present invention is not critical to success of the method, as various preparation strategies have been used with equal success.

Alternatively, the protein can be chemically synthesized, in a manner known to the art, using the amino acid sequence attached hereto as SEQ ID NO:2 as a guide. It is also possible to prepare a genetic construct that encodes the modified protein (and associated transcription and translation signals) by using standard recombinant DNA methods familiar to molecular biologists. The genetic material useful for preparing such constructs can be obtained from existing Tn5 constructs, or can be prepared using known methods for introducing mutations into genetic material (e.g., random mutagenesis PCR or site-directed mutagenesis) or some combination of both methods. The genetic sequence that encodes the protein shown in SEQ ID NO:2 is set forth in SEQ ID NO:1.

The nucleic acid and amino acid sequence of wild type Tn5 transposase are known and published. N.C.B.I. Accession Number U00004 L19385, incorporated herein by reference.

In a preferred embodiment, the improved avidity of the modified transposase for the repeat sequences for OE termini (class (1) mutation) can be achieved by providing a lysine residue at amino acid 54, which is glutamic acid in wild type Tn5 transposase. The mutation strongly alters the preference of the transposase for OE termini, as opposed to inside end ("IE") termini. The higher binding of this mutation, known as EK54, to OE termini results in a transposition rate that is about 10-fold higher than is seen with wild type transposase. A similar change at position 54 to valine (mutant EV54) also results in somewhat increased preference (about 3-fold higher than wild type) for OE termini, as does a threonine-to-proline change at position 47 (mutant TP47; about 10-fold higher). It is believed that other, comparable transposase mutations (in one or more amino acids) that increase binding avidity for OE termini may also be obtained which would function as well or better in the in vitro assay described herein.

One of ordinary skill will also appreciate that changes to the nucleotide sequences of the short repeat sequences of the donor DNA may coordinate with other mutation(s) in or near the binding region of the transposase enzyme to achieve the same increased binding effect, and the resulting 5- to 50-fold increase in transposition rate. Thus, while the applicants have exemplified one case of a mutation that improves binding of the exemplified transposase, it will be understood that other mutations in the transposase, or in the short repeat sequences, or in both, will also yield transposases that fall within the scope and spirit of the present invention. A suitable method for determining the relative avidity for Tn5 OE termini has been published by Jilk, R. A., et al., "The Organization of the Outside end of Transposon Tn5," *J. Bact.* 178:1671–79 (1996).

The transposase of the present invention is also less likely than the wild type protein to assume an inactive multimeric form. In the preferred embodiment, that class (2) mutation from wild type can be achieved by modifying amino acid 372 (leucine) of wild type Tn5 transposase to a proline (and, likewise by modifying the corresponding DNA to encode proline). This mutation, referred to as LP372, has previously been characterized as a mutation in the dimerization region of the transposase. Weinreich, et al., supra. It was noted by Weinreich et al. that this mutation at position 372 maps to a region shown previously to be critical for interaction with an inhibitor of Tn5 transposition. The inhibitor is a protein encoded by the same gene that encodes the transposase, but which is truncated at the N-terminal end of the protein, relative to the transposase. The approach of Weinreich et al. for determining the extent to which multimers are formed is suitable for determining whether a mutation falls within the scope of this element.

It is thought that when wild type Tn5 transposase multimerizes, its activity in trans is reduced. Presumably, a mutation in the dimerization region reduces or prevents multimerization, thereby reducing inhibitory activity and leading to levels of transposition 5- to 50-fold higher than are seen with the wild type transposase. The LP372 mutation achieves about 10-fold higher transposition levels than wild type. Likewise, other mutations (including mutations at a one or more amino acid) that reduce the ability of the transposase to multimerize would also function in the same manner as the single mutation at position 372, and would also be suitable in a transposase of the present invention. It may also be possible to reduce the ability of a Tn5 transposase to multimerize without altering the wild type sequence in the so-called dimerization region, for example by adding into the system another protein or non-protein agent that blocks the dimerization site. Alternatively, the dimerization region could be removed entirely from the transposase protein.

As was noted above, the inhibitor protein, encoded in partially overlapping sequence with the transposase, can interfere with transposase activity. As such, it is desired that the amount of inhibitor protein be reduced over the amount observed in wild type in vivo. For the present assay, the transposase is used in purified form, and it may be possible to separate the transposase from the inhibitor (for example, according to differences in size) before use. However, it is also possible to genetically eliminate the possibility of having any contaminating inhibitor protein present by removing its start codon from the gene that encodes the transposase.

An AUG in the wild type Tn5 transposase gene that encodes methionine at transposase amino acid 56 is the first codon of the inhibitor protein. However, it has already been shown that replacement of the methionine at position 56 has no apparent effect upon the transposase activity, but at the same time prevents translation of the inhibitor protein, thus resulting in a somewhat higher transposition rate. Weigand, T. W. and W. S. Reznikoff, "Characterization of Two Hypertransposing Tn5 Mutants," *J. Bact.* 174:1229–1239 (1992), incorporated herein by reference. In particular, the present inventors have replaced the methionine with an alanine in the preferred embodiment (and have replaced the methionine-encoding AUG codon with an alanine-encoding GCC). A preferred transposase of the present invention therefore includes an amino acid other than methionine at amino acid position 56, although this change can be considered merely technically advantageous (since it ensures the absence of the inhibitor from the in vitro system) and not essential to the invention (since other means can be used to eliminate the inhibitor protein from the in vitro system).

The most preferred transposase amino acid sequence known to the inventors differs from the wild type at amino acid positions 54, 56, and 372. The mutations at positions 54 and 372 separately contribute approximately a 10-fold increase to the rate of transposition reaction in vivo. When the mutations are combined using standard recombinant techniques into a single molecule containing both classes of mutations, reaction rates of at least about 100-fold higher than can be achieved using wild type transposase are observed when the products of the in vitro system are tested in vivo. The mutation at position 56 does not directly affect the transposase activity.

Other mutants from wild type that are contemplated to be likely to contribute to high transposase activity in vitro include, but are not limited to glutaminic acid-to-lysine at position 110, and glutamic acid to lysine at position 345.

It is, of course, understood that other changes apart from these noted positions can be made to the modified transposase (or to a construct encoding the modified transposase) without adversely affecting the transposase activity. For example, it is well understood that a construct encoding such a transposase could include changes in the third position of codons such that the encoded amino acid does not differ from that described herein. In addition, certain codon changes have little or no functional effect upon the transposition activity of the encoded protein. Finally, other changes may be introduced which provide yet higher transposition activity in the encoded protein. It is also specifically envisioned that combinations of mutations can be combined to encode a modified transposase having even higher transposition activity than has been exemplified herein. All of these changes are within the scope of the present invention. It is noted, however, that a modified transposase containing the EK110 and EK345 mutations (both described by Weigand and Reznikoff, supra, had lower transposase activity than a transposase containing either mutation alone.

After the enzyme is prepared and purified, as described supra, it can be used in the in vitro transposition reaction described above to introduce any desired transposable element from a donor DNA into a target DNA. The donor DNA can be circular or can be linear. If the donor DNA is linear, it is preferred that the repeat sequences flanking the transposable element should not be at the termini of the linear fragment but should rather include some DNA upstream and downstream from the region flanked by the repeat sequences.

The transposable element between the OE termini can include any desired nucleotide sequence. The length of the transposable element between the termini should be at least about 50 base pairs, although smaller inserts may work. No upper limit to the insert size is known. However, it is known that a donor DNA portion of about 300 nucleotides in length can function well. By way of non-limiting examples, the transposable element can include a coding region that encodes a detectable or selectable protein, with or without associated regulatory elements such as promoter, terminator, or the like.

If the element includes such a detectable or selectable coding region without a promoter, it will be possible to identify and map promoters in the target DNA that are uncovered by transposition of the coding region into a position downstream thereof, followed by analysis of the nucleic acid sequences upstream from the transposition site.

Likewise, the element can include a primer binding site that can be transposed into the target DNA, to facilitate sequencing methods or other methods that rely upon the use of primers distributed throughout the target genetic material. Similarly, the method can be used to introduce a desired restriction enzyme site or polylinker, or a site suitable for another type of recombination, such as a cre-lox, into the target.

The invention can be better understood upon consideration of the following examples which are intended to be exemplary and not limiting on the invention.

EXAMPLES

To obtain the transposase modified at position 54, the first third of the coding region from an existing DNA clone that encodes the Tn5 transposase but not the inhibitor protein (MA56) was mutagenized according to known methods and DNA fragments containing the mutagenized portion were cloned to produce a library of plasmid clones containing a full length transposase gene. The clones making up the library were transformed into *E. coli* K-12 strain MDW320 bacteria which were plated and grown into colonies. Transposable elements in the bacteria included the lacZ gene. Colonies having active transposase activity were selected by screening for blue (LacZ) spots in white colonies grown in the presence of X-gal. This population assay was described by Weinreich, et al., "A functional analysis of the Tn5 Transposase: Identification of Domains Required for DNA Binding and Dimerization," *J. Mol. Biol.* 241:166–177 (1994), incorporated herein by reference. The 5'-most third of Tn5 transposase genes from such colonies were sequenced to determine whether a mutation was responsible for the increase in transposase activity. It was determined that a mutation at position 54 to lysine (K) correlated well with the increase in transposase activity. Plasmid pRZ5412–EK54 contains lysine at position 54 as well as the described alanine at position 56.

The fragment containing the LP372 mutation was isolated from pRZ4870 (Weinreich et al (1994)) using restriction enzymes NheI and BglII, and were ligated into NheI-BglII cut pRZ5412–EK54 to form a recombinant gene having the mutations at positions 54, 56 and 372, as described herein and shown in SEQ ID NO:1. The gene was tested and shown to have at least about a one hundred fold increase in activity relative to wild type Tn5 transposase. Each of the mutants at positions 54 and 372 alone had about a 10-fold increase in transposase activity.

The modified transposase protein encoded by the triple-mutant recombinant gene was transferred into commercial T7 expression vector pET-21D (commercially available from Novagen, Madison, Wis.) by inserting a BspHI/SalI fragment into NhoI/XhoI fragment of the pET-21D vector. This cloning puts the modified transposase gene under the control of the T7 promoter, rather than the natural promoter of the transposase gene. The gene product was overproduced in BL21(DE3)pLysS bacterial host cells, which do not contain the binding site for the enzyme, by specific induction in a fermentation process after cell growth is complete. (See, Studier, F. W., et al., "Use of T7 RNA Polymerase to Direct Expression of Cloned Genes," *Methods Enzymol.* 185:60–89 (1990)). The transposase was partially purified using the method of de la Cruz, modified by inducing overproduction at 33 or 37° C. After purification, the enzyme preparation was stored at −70° C. in a storage buffer (10% glycerol, 0.7M NaCl, 20 mM Tris-HCl, pH 7.5, 0.1% TRITON-X100 and 10 mM CHAPS) until use. This storage buffer is to be considered exemplary and not optimized.

A single plasmid (pRZTL1, FIG. 1) was constructed to serve as both donor and target DNA in this Example. The complete sequence of the pRZTL1 plasmid DNA is shown and described in SEQ ID NO:3. Plasmid pRZTL1 contains two Tn5 19 base pair OE termini in inverted orientation to each other. Immediately adjacent to one OE sequence is a gene that would encode tetracycline resistance, but for the lack of an upstream promoter. However, the gene is expressed if the tetracycline resistance gene is placed downstream of a transcribed region (e.g., under the control of the promoter that promotes transcription of the chloramphenicol resistance gene also present on pRZTL1). Thus, the test plasmid pRZTL1 can be assayed in vivo after the in vitro reaction to confirm that transposition has occurred. The plasmid pRZTL1 also includes an origin of replication in the transposable element, which ensures that all transposition products are plasmids that can replicate after introduction in host cells.

The following components were used in typical 20 µl in vitro transposition reactions:

Modified transposase: 2 µl (approximately 0.1 µg enzyme/µl) in storage buffer (10% glycerol, 0.7M NaCl, 20 mM Tris-HCl, pH 7.5, 0.1% TRITON-X100 and 10 mM CHAPS)

Donor/Target DNA: 18 µl (approximately 1–2 µg) in reaction buffer (at final reaction concentrations of 0.1 M potassium glutamate, 25 mM Tris acetate, pH 7.5, 10 mM $Mg^{2+}$-acetate, 50 µg/ml BSA, 0.5 mM β-mercaptoethanol, 2 mM spermidine, 100 µg/ml tRNA).

At 20° C., the transposase was combined with pRZTL1 DNA for about 60 minutes. Then, the reaction volume was increased by adding two volumes of reaction buffer and the temperature was raised to 37° C. for 2–3 hours whereupon cleavage and strand transfer occurred.

Efficient in vitro transposition was shown to have occurred by in vivo and by in vitro methods. In vivo, many tetracycline-resistant colonies were observed after transferring the nucleic acid product of the reaction into DH5α bacterial cells. As noted, tetracycline resistance can only arise in this system if the transposable element is transposed downstream from an active promoter elsewhere on the plasmid. A typical transposition frequency was 0.1% of cells that received plasmid DNA, as determined by counting chloramphenicol resistant colonies. However, this number underestimates the total transposition event frequency because the detection system limits the target to 1/16 of the total.

Moreover, in vitro electrophoretic (1% agarose) and DNA sequencing analyses of DNA isolated from purified colonies revealed products of true transposition events, including both intramolecular and intermolecular events. Results of typical reactions using circular plasmid pRZTL1 substrates are shown in Lanes 4 & 5. Lane 6 of FIG. 2 shows the results obtained using linear plasmid pRZTL1 substrates.

The bands were revealed on 1% agarose gels by staining with SYBR Green Nucleic Acid gel strain (FMC BioProducts) and were scanned on a FLUORIMAGER SI fluorescent sample imager (Molecular Dynamics). In FIG. 2, lane 1 shows relaxed circle, linear, and closed circle versions of pRZTL1. Lanes 2 and 3 show intramolecular and intermolecular transposition products after in vitro transposition of pRZTL1, respectively. The products were purified from electroporated DH5α cells and were proven by size and sequence analysis to be genuine transposition products. Lanes 4 and 5 represent products of two independent in vitro reactions using a mixture of closed and relaxed circular test plasmid substrates. In lane 6, linear pRZTL1 (XhoI-cut) was the reaction substrate. Lane 7 includes a BstEII digest of lambda DNA as a molecular weight standard.

Figure 2:
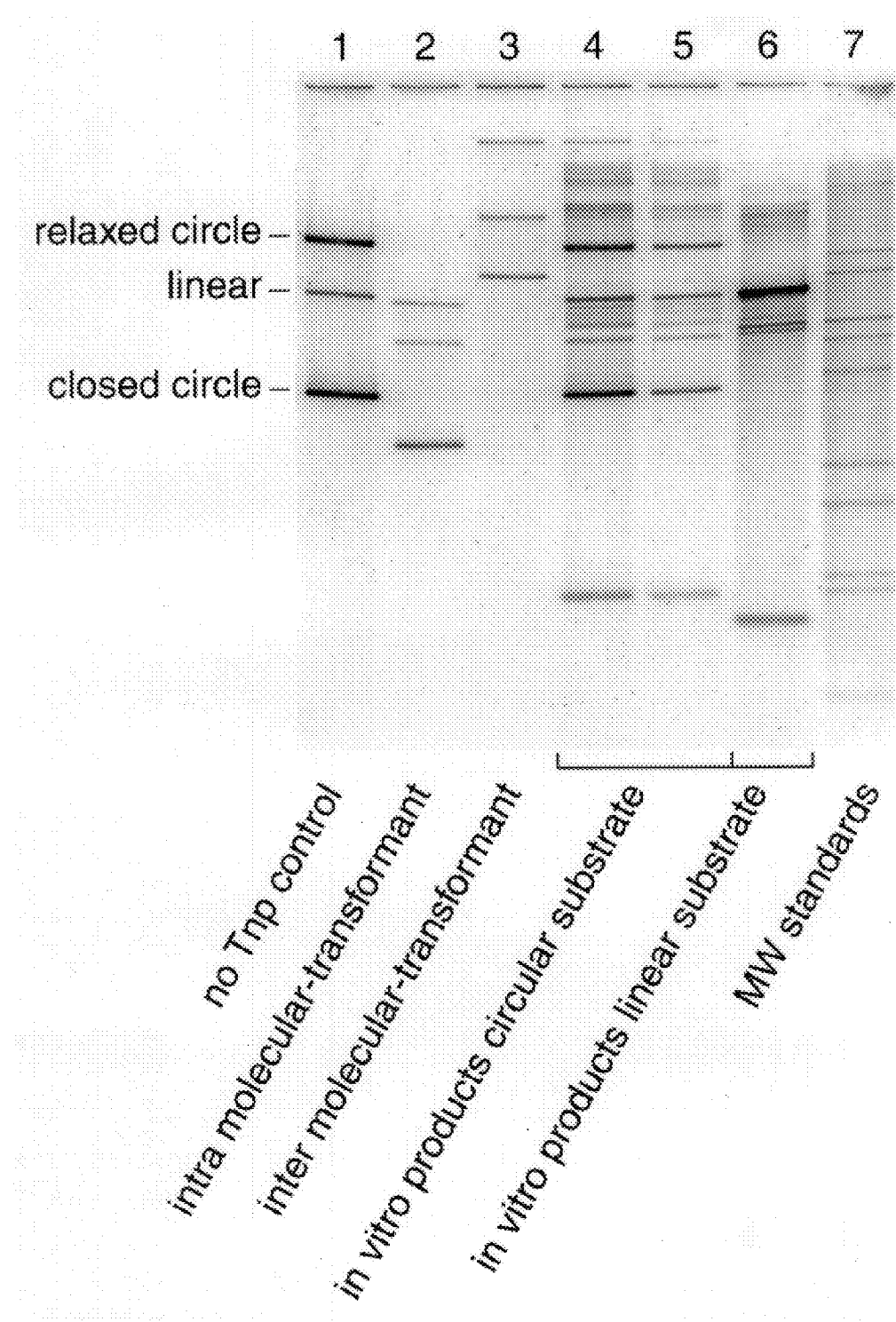
FIG. 2 depicts an electrophoretic analysis of plasmid pRZTL1 before and after in vitro transposition. Data obtained using both circular and linear plasmid substrates are shown.
Figure 3:
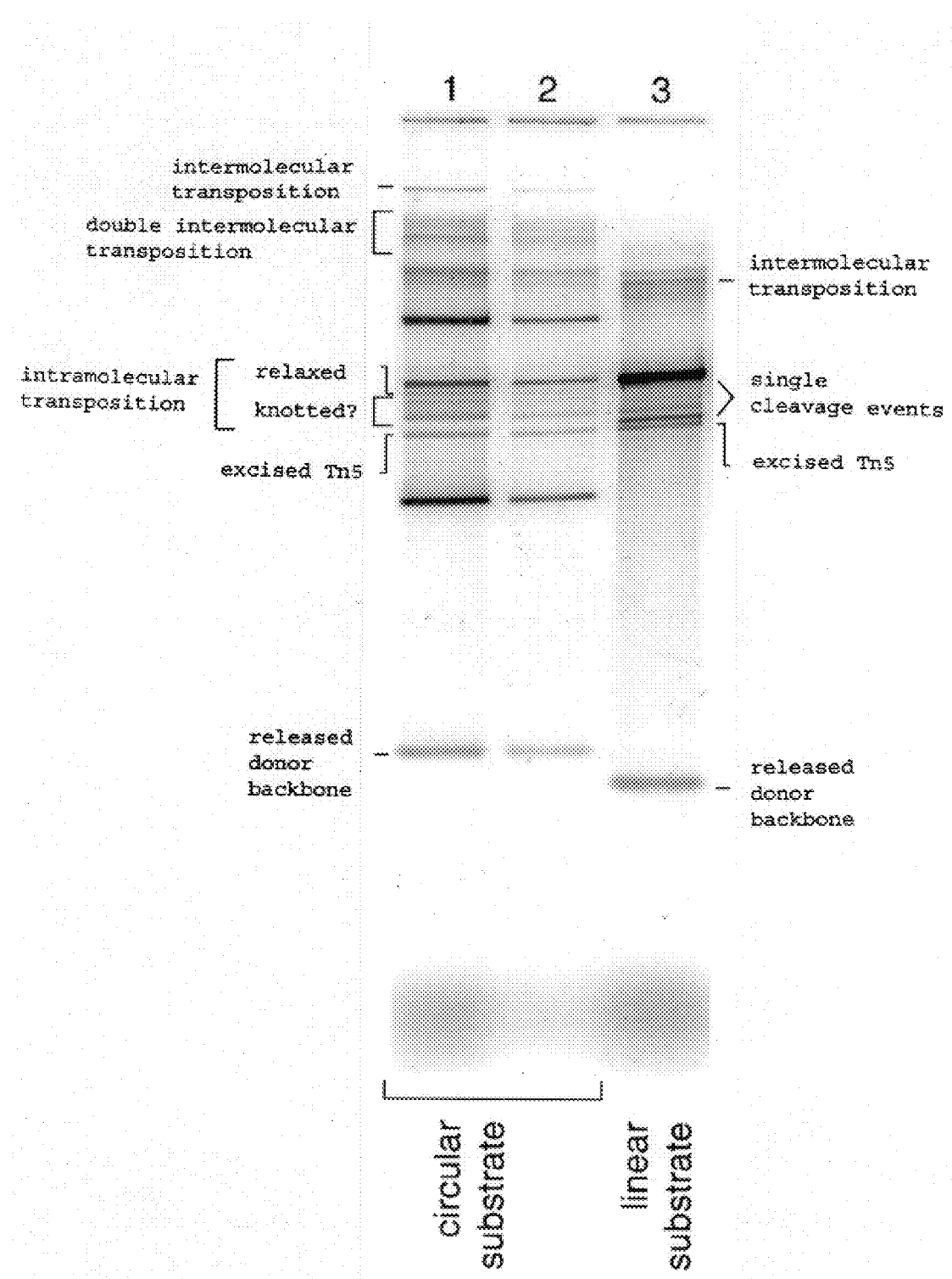
FIG. 3 is an electrophoretic analysis of plasmid pRZTL1 after in vitro transposition, including further analysis of the molecular species obtained using circular and linear plasmid substrates.

FIG. 3 reproduces lanes 4, 5, and 6 of FIG. 2 and shows an analysis of various products, based upon secondary restriction digest experiments and re-electroporation and DNA sequencing. The released donor DNA corresponds to the fragment of pRZTL1 that contains the kanamycin resistance gene between the two OE sequences, or, in the case of the linear substrate, the OE-XhoI fragment. Intermolecular transposition products can be seen only as relaxed DNA circles. Intramolecular transposition products are seen as a ladder, which results from conversion of the initial superhelicity of the substrate into DNA knots. The reaction is efficient enough to achieve double transposition events that are a combination of inter- and intramolecular events.

It is envisioned that in addition to the uses specifically noted herein, other applications will be apparent to the skilled molecular biologist. In particular, methods for introducing desired mutations into prokaryotic or eukaryotic DNA are very desirable. For example, at present it is difficult to knock out a functional eukaryotic gene by homologous recombination with an inactive version of the gene that resides on a plasmid. The difficulty arises from the need to flank the gene on the plasmid with extensive upstream and downstream sequences. Using this system, however, an inactivating transposable element containing a selectable marker gene (e.g., neo) can be introduced in vitro into a plasmid that contains the gene that one desires to inactivate. After transposition, the products can be introduced into suitable host cells. Using standard selection means, one can recover only cell colonies that contain a plasmid having the transposable element. Such plasmids can be screened, for example by restriction analysis, to recover those that contain a disrupted gene. Such clones can then be introduced directly into eukaryotic cells for homologous recombination and selection using the same marker gene.

Also, one can use the system to readily insert a PCR-amplified DNA fragment into a vector, thus avoiding traditional cloning steps entirely. This can be accomplished by (1) providing suitable a pair of PCR primers containing OE termini adjacent to the sequence-specific parts of the primers, (2) performing standard PCR amplification of a desired nucleic acid fragment, (3) performing the in vitro transposition reaction of the present invention using the double-stranded products of PCR amplification as the donor DNA.

The invention is not intended to be limited to the foregoing examples, but to encompass all such modifications and variations as come within the scope of the appended claims.

We claim:

1. A mutant Tn5 transposase modified relative to a wild type Tn5 transposase, the mutant transposase comprising:
   a mutation at position 54; and
   a mutation at position 372,
   the mutant transposase having greater avidity for Tn5 outside end repeat sequences of a donor DNA and a lesser ability to form multimers than wild type Tn5 transposase.

2. A Tn5 transposase as claimed in claim 1 wherein the mutation at position 54 is a substitution mutation.

3. A Tn5 transposase as claimed in claim 1 wherein the mutation at position 372 is a substitution mutation.

4. A Tn5 transposase as claimed in claim 3 wherein position 372 is a proline.

5. A Tn5 transposase as claimed in claim 1 further comprising a substitution mutation at position 56, wherein the mutant transposase lacks an inhibitor activity.

6. A Tn5 transposase as claimed in claim 5 wherein position 56 is alanine.

7. A mutant Tn5 transposase modified relative to a wild type Tn5 transposase, the mutant transposase comprising a mutation at position 54 ; and
   a mutation at position 372,
   the mutant transposase having greater avidity for Tn5 outside end repeat sequences of a donor DNA and a lesser ability to form multimers than wild type Tn5 transposase wherein position 54 is a lysine.

8. A system for transposing a transposable DNA sequence in vitro, the system comprising:
   a mutant Tn5 transposase modified relative to a wild type Tn5 transposase, the mutant transposase comprising a mutation at position 54, and a mutation at position 372, the mutant transposase having greater avidity for Tn5 outside end repeat sequences of a donor DNA and a lesser ability to form multimers than wild type Tn5 transposase;
   a donor DNA molecule comprising the transposable DNA sequence, the DNA sequence being flanked at its 5'-and 3' ends by the Tn5 outside end repeat sequences; and
   a target DNA molecule into which the transposable element can transpose.

9. A system as claimed in claim 8 wherein the mutation at position 54 is a substitution mutation.

10. A system as claimed in claim 8 wherein the mutation at position 372 is a substitution mutation.

11. A system as claimed in claim 10 wherein position 372 is a proline.

12. A system as claimed in claim 8 wherein the transposase further comprises a substitution mutation at position 56, wherein the mutant transposase lacks an inhibitor activity.

13. A system as claimed in claim 12 wherein position 56 is an alanine.

14. A system for transposing a transposable DNA sequence in vitro, the system comprising:
   a mutant Tn5 transposase modified relative to a wild type Tn5 transposase, the mutant transposase comprising a mutation at position 54, and a mutation at position 372, the mutant transposase having greater avidity for Tn5 outside end repeat sequences of a donor DNA and a lesser ability to form multimers than wild type Tn5 transposase;
   a donor DNA molecule comprising the transposable DNA sequence, the DNA sequence being flanked at its 5'-and 3' ends by the Tn5 outside end repeat sequences; and
   a target DNA molecule into which the transposable element can transpose
   wherein position 54 is a lysine.

15. A method for in vitro transposition, the method comprising the steps of:
   combining a donor DNA molecule that comprises a transposable DNA sequence of interest, the DNA sequence of interest being flanked at its 5'- and 3'-ends by Tn5 outside end repeat sequences, with a target DNA molecule and a mutant Tn5 transposase modified relative to wild type Tn5 transposase in a suitable reaction buffer at a temperature below a physiological temperature until the modified transposase binds to the outside end repeat sequences; and
   raising the temperature to a physiological temperature for a period of time sufficient for the enzyme to catalyze in vitro transposition,
   wherein the mutant transposase comprises a mutation at position 54 and a mutation at position 372, the mutant transposase having greater avidity for Tn5 outside end repeat sequences of a donor DNA and a lesser ability to form multimers than wild type Tn5 transposase.

16. A method as claimed in claim 15 wherein the mutation at position 54 is a substitution mutation.

17. A method as claimed in claim 15 wherein the mutation at position 372 is a substitution mutation.

18. A method as claimed in claim 17 wherein position 372 is a proline.

19. A method as claimed in claim 15 wherein the transposase further comprises a substitution mutation at position 56, wherein the mutant transposase lacks an inhibitor activity.

20. A method as claimed in claim 19 wherein position 56 is an alanine.

21. A method for in vitro transposition, the method comprising the steps of:
   combining a donor DNA molecule that comprises a transposable DNA sequence of interest, the DNA sequence of interest being flanked at its 5'- and 3'-ends by Tn5 outside end repeat sequences, with a target DNA molecule and a mutant Tn5 transposase modified relative to wild type Tn5 transposase in a suitable reaction buffer at a temperature below a physiological temperature until the modified transposase binds to the outside end repeat sequences; and raising the temperature to a physiological temperature for a period of time sufficient for the enzyme to catalyze in vitro transposition, wherein the mutant transposase comprises a mutation at position 54 and a mutation at position 372, the mutant transposase having greater avidity for Tn5 outside end repeat sequences of a donor DNA and a lesser ability to form multimers than wild type Tn5 transposase wherein position 54 is a lysine.

\* \* \* \* \*